(12) United States Patent
Moloney et al.

(10) Patent No.: US 6,503,933 B1
(45) Date of Patent: Jan. 7, 2003

(54) 2-PYRIDYLMETHYLAMINE DERIVATIVES USEFUL AS FUNGICIDES

(75) Inventors: Brian Anthony Moloney, Essex (GB); David Hardy, Essex (GB); Elizabeth Anne Saville-Stones, Essex (GB)

(73) Assignee: Aventis CropScience UK Limited (GB)

( * ) Notice: Subject to any disclaimer, the term of this patent is extended or adjusted under 35 U.S.C. 154(b) by 0 days.

(21) Appl. No.: 09/622,651

(22) PCT Filed: Feb. 16, 1999

(86) PCT No.: PCT/GB99/00304

§ 371 (c)(1),
(2), (4) Date: Sep. 21, 2000

(87) PCT Pub. No.: WO99/42447

PCT Pub. Date: Aug. 26, 1999

(30) Foreign Application Priority Data

| Feb. 19, 1998 | (GB) | ............................................... 9803413 |
| Jun. 30, 1998 | (GB) | ............................................... 9813998 |
| Aug. 11, 1998 | (GB) | ............................................... 9817353 |

(51) Int. Cl.⁷ ...................... A61K 31/44; C07D 211/70; C07D 211/78; C07D 211/72

(52) U.S. Cl. ...................... 514/357; 546/337; 546/287; 546/291; 546/307; 546/330; 514/345; 514/353

(58) Field of Search ................................. 546/336, 331, 546/337, 287, 291, 307, 330; 514/357, 345, 353

(56) References Cited

FOREIGN PATENT DOCUMENTS

| DE | 2417763 | 10/1975 |
| DE | 4434637 | 4/1996 |
| EP | 0262393 | 4/1988 |
| EP | 0356234 | 2/1990 |
| EP | 0356234 | * 8/1999 |
| WO | 9805961 | * 2/1998 |

OTHER PUBLICATIONS

CA reference 68:59410, "New compounds. Amides derived from 2–(2–pyridyl)ethylamines", Sam et. al., vol. 68, p. 5737, 1968.*

Egner, et. al., "Design of Inhibitors of photsystem II using a modle of the D1 protein", Pestic. Sci. (1996), 47(2), pp. 145–158.*

Buhleier et. al., "Ligand structure and complexation, XXII. 2, 6–Bis(aminomethyl)pyridine as a complex ligand and new building block for crown ether synthesis", Justus Liebigs Ann. Chem. (1978), (4), pp. 537–544.*

* cited by examiner

Primary Examiner—Alan L. Rotman
Assistant Examiner—Binta Robinson
(74) Attorney, Agent, or Firm—Ostrolenk, Faber, Gerb & Soffen, LLP

(57) ABSTRACT

Compounds of formula (I) and salts thereof as phytopathogenic fungicides wherein $A^1$ is substituted 2-pyridyl; $A^2$ is optionally substituted phenyl; L is —(C=O)—, —SO$_2$— or —(C=S)—; $R^1$ is hydrogen, optionally substituted alkyl or acyl; and $R^2$ is hydrogen or optionally substituted alkyl are useful phytopathogenic fungicides.

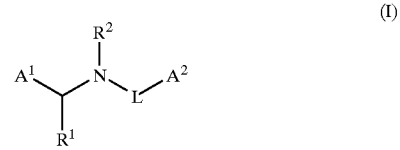

(I)

9 Claims, No Drawings

2-PYRIDYLMETHYLAMINE DERIVATIVES USEFUL AS FUNGICIDES

This invention relates to compounds having fungicidal activity, their preparation, and intermediates for their preparation.

In a first aspect the invention provides the use of compounds of formula I and salts thereof as phytopathogenic fungicides

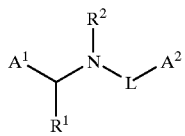

(I)

wherein
- $A^1$ is substituted 2-pyridyl;
- $A^2$ is optionally substituted phenyl;
- L is —(C=O)—, —SO$_2$— or —(C=S)—;
- $R^1$ is hydrogen, optionally substituted alkyl or acyl; and
- $R^2$ is hydrogen or optionally substituted alkyl.

The 2-pyridyl group ($A^1$) can have up to four substituents, preferably up to two, which may be the same or different to each other. Preferably, the substituents are on the 3 and/or 5 position of the 2-pyridyl group.

Preferred substituents on the 2-pyridyl group ($A^1$) are halogen, hydroxy, cyano, nitro, $SF_5$, trialkylsilyl, optionally substituted amino, acyl, or a group E, OE or SE, where E is alkyl, alkenyl, alkynyl, cycloalkyl, cycloalkenyl, phenyl or heterocyclyl, each of which is optionally substituted, or a group —C(E)=N—Q, where Q is E, OE, SE or optionally substituted amino: or two adjacent substituents together with the atoms-to which they are attached form an optionally substituted ring which can contain up to 3 hetero atoms. Especially preferred substituents are alkoxy, alkyl, cyano, halogen, nitro, alkoxycarbonyl, alkylsulfinyl, alkylsuffonyl and trifluoromethyl, particularly chlorine and trifluoromethyl.

The phenyl group, $A^2$. may have up to five substituents, preferably up to 3, especially up to two, which may De the same or different to each other. Preferred substituents are the same as those defined for $A^1$ above. Particularly preferred substituents are alkoxy, alkyl, halogen, nitro or trifluoromethyl.

Preferably the linking group L is —(C=O)—.

$R^1$ is preferably hydrogen. When it is not hydrogen, it is preferably alkyl, optionally substituted by phenyl, or alkoxycarbonyl.

Many of the compounds of formula I are novel. Therefore according to a second aspect, the invention provides compounds of formula I where $A^1$ is a 2-pyridyl group having substituents at the 3 and/or 5 position and no other position, $R^1$ and $R^2$ are hydrogen and $A^2$ and L are as defined above.

The invention also includes any of the compounds specifically exemplified hereinafter.

Any alkyl group present in the molecule is preferably of 1 to 10 carbon atoms, especially of 1 to 7 carbon atoms, and particularly of 1 to 5 carbon atoms.

Any alkenyl or alkynyl group present in the molecule is preferably of 2 to 7 carbon atoms, for example allyl, vinyl or propargyl.

Any cycloalkyl, cycloalkenyl or cycloalkynyl group present in the molecule is preferably of 3 to 7 carbon atoms, especially cyclopropyl, cyclopentyl, cyclohexyl or cyclohexenyl.

Substituents, when present on any alkyl, alkenyl, alkynyl, cycloalkyl, cycloalkenyl cycloalkynyl moiety may for example be halogen, cyano, optionally substituted alkoxy, optionally substituted alkylthio, mercapto, hydroxy, nitro, optionally substituted amino, acyl, acyloxy, acylthio, optionally substituted phenyl, optionally substituted heterocyclyl, optionally substituted phenylthio, optionally substituted phenoxy, optionally substituted heterocyclyloxy or optionally substituted heterocyclylthio.

Preferred substituents on any alkyl, alkenyt or alkynyl group are alkoxy, haloalkoxy or alkylthio, each containing 1 to 5 carbon atoms, halogen; or optionally substituted phenyl. An especialy preferred group ism trifluoromethyls Cycmoalkyl, cycloalkenyl, cycloalkynyl groups may also be substituted by optionally substituted alkyl, alkynyl or alkenyl and vice versa.

Substituents when present on any phenyl or heterocyclyl group are preferably as defined above for substituents on $A^2$.

The term heterocyclyl includes both aromatic and non-aromatic heterocyclyl groups. Heterocyclyl groups are generally 5, 6 or 7-membered rings containing up to 4 hetero atoms selected from nitrogen, oxygen and sulfur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, triazinyl, thiazolinyl, benzimidazolyl, tetrazolyl, benzoxazolyl, imidazopyridinyl, 1,3-benzoxazinyl, 1,3-benzothiazinyl, oxazolopyridinyl, benzofuranyl, quinolinyl, quinazolinyl, quinoxalinyl, sulfolanyl, dihydroquinazolinyl, benzothiazolyl, phthalimido, benzofuranyl, azepinyl, oxazepinyl, thiazepinyl, diazepinyl and benzodiazepinyl.

Amino groups may be substituted for example by one or two E or acyl groups, each of which may be the same or different, or two substituents together with the nitrogen to which they are attached can form a ring, preferably a 5 to 7-membered ring, which may be substituted and may contain other heteroatoms, for example morpholine, thiomorpholine, or piperidine. This ring can be substituted as for A.

The term acyl includes the residue of sulfur and phosphorus-containing acids as well as carboxylic acids. Examples of acyl groups are thus $COR^{5a}$, $COOR^{5a}$, $CXNR^{5a}R^{6a}$, —CON($R^{5a}$)OR$^{6a}$, —COONR$^{5a}R^{6a}$, —CON($R^{5a}$)NR$^{6a}R^{7a}$, —COSR$^{5a}$, —CSSR$^{5a}$, —S(O)$_y$R$^{5a}$, —S(O)$_2$OR$^{5a}$, —S(O)$_y$NR$^{5a}R^{6a}$, —p(=X)(OR$^{5a}$)(OR$^{6a}$), —CO—COOR$^{5a}$ where $R^{5a}$, $R^{6a}$ and $R^{7a}$, which may be the same or different, are hydrogen, optionally substituted alkyl, optionally substituted alkenyl, optionally substituted alkynyl, optionally substituted cycloalkyl, optionally substituted cycloalkenyl, optionally substituted cycloalkynyl optionally substituted phenyl or optionally substituted heterocyclyl, or $R^{5a}$ and $R^{6a}$, or $R^{6a}$ and $R^{7a}$, together with the atom(s) to which they are attached can form a ring, y is 1 or 2 and X is O or S.

When substituted, substituents on the phenyl and alkyl groups are as defined above.

In preferred compounds of the invention
- $A^1$ is a mono- or disubstituted 2-pyridyl group, substituted by chlorine and/or trifluoromethyl at the 3 and/or 5 position, e.g. 2-(5-chloro-3-trifluoromethyl)pyridyl;
- X is —C(=O)—; and
- $R^1$ is hydrogen or alkyt, e.g. methyl, and especially hydrogen; and R² is hydrogen, alkyl, (e.g. methyl), benzyl or alkoxycarbonyl, (e.g. ethoxycarbonyl) and especially hydrogen.

Particularly preferred substituents on the A² phenyl are halogen.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondite*), late tomato or potato blight (*Phytophthora infestans*), apple scab (*Venturia inaequalis*), glume blotch (*Leptosphaeria nodorum*). Other fungi against which the compounds may be active include other powdery mildews, other rusts, and general pathogens of Deuteromycete, Ascomycete, Phycomycete and Basidiomycete origin.

The invention thus also provides a method of combating fungi at a locus infested or tiable to be infested therewith. which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition the composition can comprise one or more additional active ingredients, for example compounds known to possess plant-growth regulant, herbicidal, fungicidal, insecticidal or acaricidal properties. Alternatively the compound of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters: fatty alcohol sulfates such as sodium dodecyl sulfate, sodium octadecyl sulfate or sodium cetyl sulfate; ethoxylated fatty alcohol sulfates; ethoxylated aikylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine or the diatkyl sulfosuccinates, e.g. the sodium sulfonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

In the method of the invention the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

In addition, the compounds of the invention can be applied to plants or parts thereof which have been genetically modified to exhibit a trait such as fungal, insect, and/or herbicidal resistance.

The compounds of formula I may be obtained by reacting a compound of formula II, or its hydrochloride salt, with a compound of formula III according to Scheme 1, where X is a leaving group such as nalogen. When is —(C=O)— or —SO$_2$—, preferred reaction conditions comprise mixing II with the corresponding benzoyl or subfonyl chloride in the presence of triethylamine.

Scheme 1

$$A^1\underset{R^1}{\overset{R^2}{\diagdown}}NH \quad + \quad A^2\text{—L—X} \quad \longrightarrow \quad A^1\underset{R^1}{\overset{R^2}{\diagdown}}N\underset{L}{\diagdown}A^2$$

(II)        (III)        (I)

Compounds of formula I where R$^2$ is optionally substituted alkyl can be prepared by alkylating, in known manner, compounds of formula I where R$^2$ is hydrogen.

Compounds of formula III are known or can be obtained in known manner.

Certain compounds of intermediate formula IIa below, are known, i.e. compounds of general formula II where R$^1$ and R$^2$ are hydrogen. However the art contains no high-yielding, preparative method for compounds of formula IIa. We have now developed such a method.

Therefore, according to a third aspect, the invention provides a process for preparing compounds of formula ha comprising the steps of:

a) reacting under basic conditions, compounds of formula IV, with compounds of formula V to give intermediates of formula VI, $$\underset{E^1}{\diagdown}N=\underset{R^b}{\overset{R^a}{\diagup}} \quad + \quad A^1\text{—}X^1 \quad \longrightarrow \quad A^1\underset{E^1}{\diagdown}N=\underset{R^b}{\overset{R^a}{\diagup}}$$

(IV)        (V)        (VI)

b) converting intermediates of formula VI to intermediates of formula VII, $$A^1\underset{E^1}{\diagdown}N=\underset{R^b}{\overset{R^a}{\diagup}} \quad \longrightarrow \quad A^1\underset{E^1}{\diagdown}NH_2$$

(VI)        (VII)

c) converting intermediates of formula VII to compounds of formula IIa.

$$A^1\underset{E^1}{\diagdown}NH_2 \quad \longrightarrow \quad A^1\underset{H}{\diagdown}NH_2$$

(VII)        (IIa)

wherein

R$^{5a}$ and R$^b$, which may be the same or different, are alkyl, alkenyl, alkynyl, cycloalkyl, cycloalkenyl, heterocyclyl or phenyl, each of which may be substituted (preferably optionally substituted phenyl) or hydrogen;

E$^1$ is both an electron withdrawing group and a group which may be reglaced by hydrogen using methodology known to the skilled chemist in accordance with step c) (preferably a carboxy group or a carboxy ester group);

X$^1$ is a leaving group (preferably halogen); and

A$^1$ and R$^1$ are as defined above for the first aspect of the invention.

Preferred basic conditions for step a) comprise reaction with an alkali metal hydride, alkoxide or carbonate.

Preferred, reaction conditions for step b) comprises treatment with dilute acid, particularly dilute hydrochloric acid.

When E$^1$ is a carboxy group or carboxy ester group, suitable reaction conditions for decarboxylation [step c)] will be known to the skilled chemist. Preferred decarboxylation conditions comprise heating VII with dilute aqueous hydrochloric acid.

Compounds of formula IIV are known or can be prepared in known manner.

Intermediates VI and VII may be isolated. Alternatively they may be generated in situ and the subsequent reaction step performed without isolation or purification. It is preferred that intermediate VI is generated in situ, whereas it is preferred that intermediate VII is isolated.

Throughout this specification, unless the context requires otherwise, the word "comprise", or variations such as "comprises" or "comprising", will be understood to imply the inclusion of a stated integer or group of integers, but not the exclusion of any other integer or group of integers, including method steps.

The hydrochloride salt of compounds of formula IIb, i.e. compounds of general formula II where R$^1$ is optionally substituted alkyl and R$^2$ is hydrogen, may be prepared according to reaction Scheme 2. X$^2$ is a leaving group such as bromine and the base is preferably potassium tert-butoxide. Preferred reaction conditions for conversion to the hydrochloride salt of fib is treatment with dilute hydrochloric acid.

Scheme 2

$$A^1\diagdown NH_2\cdot HCl \quad \xrightarrow{Ph_2C=NH}$$

$$A^1\diagdown N\diagup\underset{Ph}{\overset{Ph}{}} \quad \xrightarrow{\begin{array}{c}1)\ base\\2)\ R^1X^2\end{array}}$$

$$A^1\underset{R^1}{\diagdown}N\diagup\underset{Ph}{\overset{Ph}{}} \quad \xrightarrow{acid}$$

$$A^1\underset{R^1}{\diagdown}NH_2\cdot HCl$$

Many of the compounds of formula IIb and their hydrochloride salts are novel. Therefore, according to a fourth aspect the invention provides a compound of formula IIb, and salts thereof,

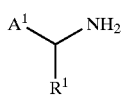

(IIb)

wherein A¹ is as defined above and R¹ is optionally substituted alkyl.

The 2-pyridyl group (A¹) can have up to four substituents, preferably up to two, which may be the same or different to each other. Preferably, the substituents are on the 3 and/or 5 position of the 2-pyridyl group.

When substituted, preferred substituents on the 2-pyridyl group (A¹) in formula IIb are halogen, hydroxy, cyano, nitro, $SF_5$, trialkylsilyl, optionally substituted amino, acyl, or a group E, OE or SE, where E is alkyl, alkenyl, alkynyl, cycloalkyl, cycloalkenyl, phenyl or heterocyclyl, each of which is optionally substituted, or a group —C(E)=N—Q, where Q is E, OE, SE or optionally substituted amino; or two adjacent substituents together with the atoms to which they are attached form an optionally substituted ring which can contain up to 3 hetero atoms. Especially preferred substituents are alkoxy, alkyl, halogen, nitro and trifluoromethyl, particularly chlorine and trifluoromethyl.

Preferably, A¹ is a mono- or di-substituted 2-pyridyl group, substituted by chlorine and/or trifluoromethyl.

The invention is illustrated in the following Examples. Structures of isolated novel compounds were confirmed by NMR and/or other appropriate analyses.

EXAMPLE 1

N-[(3-Chloro-5-trifluoromethyl-2-pyridyl)methyl]-α, α,α-trifluoro-o-toluamide (Compound 1)

A solution of (3-chloro-5-trifluoromethyl-2-pyridyl) methylamine (0.35 g) in dry ether (2 ml) was added to a solution of 2-trifluoromethylbenzoyl chloride (0.39 g) and triethylamine (0.27 ml) in dry ether (5 ml) and the mixture stirred overnight. Water (20 ml) and ethyl acetate (10 ml) were added and the organic phase was separated and washed with aqueous sodium hydrogen carbonate, dried and evaporated under reduced pressure. The residue was purified by silica gel chromatography to give the title product, m.p. 127–30° C.

EXAMPLE 2

N-[(3-Chloro-5-trifluoromethyl-2-pyridyl)methyl]-N-methyl-2,6-dichlorobenzamide (Compound 63)

Sodium hydride (0.077 g of a 60% dispersion in oil) was added, with stirring, to a solution of compound 21 (see in table below) in dry tetrahydrofuran and under nitrogen at room temperature. The mixture was warmed to 30° C. and after 10 minutes was stirred at room temperature for 30 minutes. Methyl iodide (0.12 ml) was added and the mixture stirred at room temperature overnight. The mixture was quenched by the addition dropwise of a solution of methanol in tetrahydrofuran followed by water. The tetrahydrofuran was removed by evaporation under reduced pressure and the residue was partitioned between water and ether. The aqueous layer was extracted twice with ether and the combined extracts were washed with water and then brine and dried. The extract was evaporated under reduced pressure to give the title product, m.p. 83–4° C.

EXAMPLE 3

N-[(3,5-dichloro-2-pyridyl)methyl]-2,6-dichlorobenzamide (Compound 59)

To a stirred solution of the product from stage b) (see below) (0.30 g) and triethylamine (0.4 ml) in tetrahydrofuran (5 ml) was added 2,6-dichlorobenzoyl chloride (0.2 ml) dropwise at room temperature, and stirring was continued for 12 hours. The reaction mixture was concentrated, water was added (10 ml) and the mixture was stirred for 15 minutes. The mixture was filtered and the resulting solid washed with water and then with light petroleum (b.p. 40–60° C.). The solid was recrystallised from diisopropyl ether to give the title product, m.p. 161–5° C.

Preparation of Starting Materials a) Ethyl 2-(3,5-dichloro-2-pyridyl)glycinate

To a stirred solution of sodium hydride (0.445 g) in dry dimethylformamide (4 ml) at 0° C. was added ethyl N-(diphenylmethylene)glycinate (1.485 g) in dry dimethylformamide (3 ml) and stirring was continued for 20 minutes. 2,3,5-Trichloropyridine (1.58 g) in dry dimethylformamide (4 ml) was then added dropwise over 10 mins at 5° C. and the reaction mixture was stirred for 2 hours at room temperature. 2M hydrochloric acid (25 ml) was added and stirring continued for 2 hours. The solution was washed with diethyl ether and the layers were separated. The aqueous phase was neutralised with saturated aqueous sodium bicarbonate and extracted with ethyl acetate. The combined ethyl acetate layers were washed with brine (×2), dried ($MgSO_4$), filtered and the solvent removed to leave a residue which was purified by silica gel chromatography eluting with ethyl acetate/light petroleum (40–60° C.) to give the title product.

b) (3,5-Dichloro-2-pyridyl)methylamine Hydrochloride

A mixture of the product from stage a) (0.24 g) and 3M hydrochloric acid (20 ml) was heated under reflux for 4 hours. On cooling the mixture was washed with diethyl ether and the layers separated. Water was removed from the aqueous phase by azeotropic evaporation with toluene (×3) to give the title product.

EXAMPLE 4

N-[1-(3-Chloro-5-trifluoromethyl-2-pyridyl)-2-phenylethyl]-2,6-dichlorobenzamide (Compound 83)

To a solution of the product from stage c) (see below) (0.31 g) in dichloromethane (10 ml) was added triethylamine (0.28 ml) followed by 2,6-dichlorobenzoyl chloride (0.15 ml). The mixture was stirred at room temperature for 1.5 hours and then evaporated to dryness. Diethyl ether (20 ml) was added and the solution was washed with 2M hydrochloric acid (10 ml), then water (10 ml), then sodium bicarbonate solution (10 ml) followed by water (10 ml). The organic layer was separated, dried ($MgSO_4$) and the solvent removed. The residue was purified by silica gel chromatography (light petroleum (b.p. 40–60° C.):diethyl ether (1:1)] to give the title product as a solid, m.p. 164–8° C.

Preparation of Starting Materials a) N-[(3-chloro-5-trifluoromethyl-2-pyridyl)methyl]benzophenone Imine To a solution of benzophenone imine (1.67 ml) in dry dichloromethane (25 ml) at 10° C. was added (3-chloro-5-trifluoromethyl-2-pyridyl)methylamine hydrochloride (2.47 g). The solution was stirred at room temperature for 3 hours and then filtered. The filtrate was evaporated to dryness and purified by silica gel chromatography [light petroleumidiethyl ether (4:1)] to give the title product.

b) N-[1-(3-Chloro-5-trifluoromethyl-2-pyridyl)-2-phenylethyl]benzophenone Imine

To a solution of potassium tert-butoxide (0.33 g) in tetrahydrofuran (5 ml) at −60° C. was added the product from stage a) in tetrahydrofuran (10 ml). After stirring at −60° C. for 10 minutes, benzyl bromide (0.36 ml) in dry tetrahydrofuran (20 ml) was added dropwise at −50° C. The solution was allowed to slowly attain room temperature and stirring continued overnight. The mixture was evaporated to dryness and diethyl ether (35 ml) and acetic acid (2 ml) were added. The mixture was washed with water (3×10 ml) and the phases were separated. The organic phase was dried ($MgSO_4$) and the solvent removed to give the title product.

c) 1-(3-Chloro-5-trifluoromethyl-2-pyridyl)-2-phenylethylamine Hydrochloride

To a solution of the product from stage b) (1.29 g) in diethyl ether (5 ml) was added 1 M hydrochloric acid (10 ml) at room temperature and the solution was stirred at room temperature for 2 hours. The mixture was filtered to give a solid, which was washed with water (15 ml) then ether (15 ml). Drying in vacuo gave the title product. Water was removed from the aqueous phase by azeotropic distillation with toluene (×3), to give further quantities of the title product.

In a similar manner to one of the previous Examples, the following compounds of general formula Ia were obtained. The table includes the compounds described in the previous Examples

TABLE 1

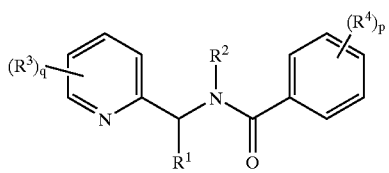

(Ia)

| Cpd | $R^1$ | $R^2$ | $(R^3)_q$ | $(R^4)_p$ | m.p. (° C.) |
|---|---|---|---|---|---|
| 1 | H | H | 3-Cl, 5-$CF_3$ | 2-$CF_3$ | 127–30 |
| 2 | H | H | 3-Cl, 5-$CF_3$ | 2-succinimido | 173–4 |
| 3 | H | H | 3-Cl, 5-$CF_3$ | 3-Br | 88 |
| 4 | H | H | 3-Cl, 5-$CF_3$ | 3,5-$Cl_2$ | 138–9 |
| 5 | H | H | 3-Cl, 5-$CF_3$ | 3,4-$Cl_2$ | 147–50 |
| 6 | H | H | 3-Cl, 5-$CF_3$ | 2,5-$Cl_2$ | 123 |
| 7 | H | H | 3-Cl, 5-$CF_3$ | 2,4-$Cl_2$ | 128 |
| 8 | H | H | 3-Cl, 5-$CF_3$ | 2,3-$Cl_2$ | 146–7 |
| 9 | H | H | 3-Cl, 5-$CF_3$ | 2,4-$(OMe)_2$ | 166 |
| 10 | H | H | 3-Cl, 5-$CF_3$ | 3-$OPr^i$ | 98–100 |
| 11 | H | H | 3-Cl, 5-$CF_3$ | 2-OCOMe | 100–4 |
| 12 | H | H | 3-Cl, 5-$CF_3$ | 4-$Bu^t$ | 139–41 |
| 13 | H | H | 3-Cl, 5-$CF_3$ | 2-$NO_2$ | 137–40 |
| 14 | H | H | 3-Cl, 5-$CF_3$ | 2,6-$F_2$ | 152–4 |
| 15 | H | H | 3-Cl, 5-$CF_3$ | 2,4-$F_2$ | 135 |
| 16 | H | H | 3-Cl, 5-$CF_3$ | 4-Cl | 108–10 |
| 17 | H | H | 3-Cl, 5-$CF_3$ | 2,3-$Me_2$ | 158 |
| 18 | H | H | 3-Cl, 5-$CF_3$ | 2-F | 116–7 |
| 19 | H | H | 3-Cl, 5-$CF_3$ | 2-Me | 135–6 |
| 20 | H | H | 3-Cl, 5-$CF_3$ | 2-Br | oil |
| 21 | H | H | 3-Cl, 5-$CF_3$ | 2,6-$Cl_2$ | 130–3 |
| 22 | H | H | 3-Cl, 5-$CF_3$ | 2-OMe | 140–4 |
| 23 | H | H | 3-Cl, 5-$CF_3$ | 2-Cl | 77–80 |
| 24 | H | H | 3-Cl, 5-$CF_3$ | — | 98–100 |
| 25 | H | H | 5-$CF_3$ | 2,6-$Cl_2$ | 152–3 |
| 26 | H | H | 3-Cl, 5-$CF_3$ | 2,6-$Me_2$ | 123 |
| 27 | H | H | 3-Cl, 5-$CF_3$ | 2,3-$F_2$ | 88–91 |
| 28 | H | H | 3-Cl, 5-$CF_3$ | 2,4,6-$Me_3$ | 146–9 |
| 29 | H | H | 3-Cl, 5-$CF_3$ | 2,3-$(CH)_4$— | 138–140 |
| 30 | H | H | 3-Cl, 5-$CF_3$ | 2-Cl-4-F | 111–3 |
| 31 | H | H | 3-Cl, 5-$CF_3$ | 2-Cl-6-F | 152–3 |
| 32 | H | H | 3-Cl, 5-$CF_3$ | 2,4,6-$F_3$ | 126–8 |
| 33 | H | H | 3-Cl, 5-$CF_3$ | 2,3,6-$F_3$ | 129 |
| 34 | H | H | 3-Cl, 5-$CF_3$ | 2,6-$(OMe)_2$ | 151 |
| 35 | H | H | 3-Cl, 5-$CF_3$ | 2-$OCF_3$ | 89–90 |
| 36 | H | H | 3-Cl, 5-$CF_3$ | 3-$CF_3$ | 133–4 |
| 37 | H | H | 3-Cl, 5-$CF_3$ | 2-Cl, 4-$NO_2$ | 147–9 |
| 38 | H | H | 3-Cl, 5-$CF_3$ | 4-Ph | 146–8 |
| 39 | H | H | 3-Cl, 5-$CF_3$ | 2-F, 6-$CF_3$ | 118–120 |
| 40 | H | H | 3-Cl, 5-$CF_3$ | 2-F, 3-$CF_3$ | 102–5 |
| 41 | H | H | 3-Cl, 5-$CF_3$ | 3-F, 6-$CF_3$ | 134–6 |
| 42 | H | H | 3-Cl, 5-$CF_3$ | 4-F, 2-$CF_3$ | 100–3 |
| 43 | H | H | 3-Cl, 5-$CF_3$ | $F_5$ | 99–101 |
| 44 | H | H | 3-Cl, 5-$CF_3$ | 2-I | 118–9 |
| 45 | H | H | 3-Cl, 5-$CF_3$ | 2-Br, 5-OMe | 122–5 |
| 46 | H | H | 3-Cl, 5-$CF_3$ | 2,6-$(CF_3)_2$ | semi-solid |
| 47 | H | Me | 5-$CF_3$ | 2,6-$Cl_2$ | 89–94 |
| 48 | H | Et | 5-$CF_3$ | 2,6-$Cl_2$ | 82–3 |
| 49 | H | H | 5-$CF_3$ | 2-Cl | 91–3 |
| 50 | H | H | 5-$CF_3$ | 2-F | 64–6 |
| 51 | H | H | 5-$CF_3$ | 2-OMe | 86–9 |
| 52 | H | H | 5-$CF_3$ | 2-$CF_3$ | 128–130 |
| 53 | H | H | 5-$CF_3$ | 2-$NO_2$ | 124–6 |
| 54 | H | H | 5-$CF_3$ | 2,6-$F_2$ | 122–4 |
| 55 | H | H | 5-$CF_3$ | 2,3-$Me_2$ | 103–6 |
| 56 | H | H | 5-$CF_3$ | 4-Cl | 107–10 |
| 57 | H | H | 5-$CF_3$ | 2-Br | 116–9 |
| 58 | H | H | 3-Cl, 5-$CF_3$ | 2,4,6-$Cl_3$ | 152–3 |
| 59 | H | H | 3,5-$Cl_2$ | 2,6-$Cl_2$ | 161–5 |
| 60 | H | H | 5-Cl | 2,6-$Cl_2$ | 129–32 |
| 61 | H | H | 3-Cl, 5-$CF_3$ | 4-$NMe_2$ | 143–4 |
| 62 | H | H | 5-Cl | 2-$NO_2$ | 129–32 |
| 63 | H | Me | 3-Cl, 5-$CF_3$ | 2,6-$Cl_2$ | 83–4 |
| 64 | H | H | 3-Cl, 5-$CF_3$ | 2-$NO_2$, 4-Me | 138–9 |
| 65 | H | H | 3-Cl, 5-$CF_3$ | 2-OPh | 97–9 |
| 66 | H | H | 3-Cl, 5-$CF_3$ | 2-Cl, 6-Br | 144–6 |
| 67 | H | H | 3-Cl, 5-$CF_3$ | 2-$NO_2$, 3-Cl | 118–9 |
| 68 | H | H | 3-Cl, 5-$CF_3$ | 2-$NO_2$, 5-Cl | 143–4 |
| 69 | H | H | 3-Cl, 5-$CF_3$ | 2-F, 6-I | 133–5 |
| 70 | H | H | 3-Cl, 5-$CF_3$ | 2-SMe | 116–7 |
| 71 | H | H | 3-Cl, 5-$CF_3$ | 2,3,5,6-$F_4$ | 112–4 |
| 72 | H | H | 3-Cl, 5-$CF_3$ | 2-Ph | 117–8 |
| 73 | H | H | 3-Cl, 5-$CF_3$ | 2-F, 3-Me | 120–1 |
| 74 | H | H | 3-Cl, 5-$CF_3$ | 2-Me, 4-Br | 107–8 |
| 75 | H | H | 3-Cl, 5-$CF_3$ | 2-Cl, 5-Br | 119–20 |
| 76 | H | H | 3-Cl, 5-$CF_3$ | 2-OMe, 5-Cl | 181–2 |
| 77 | H | H | 3-Cl, 5-$CF_3$ | 2-Cl, 5-$NO_2$ | 143–4 |
| 78 | H | H | 3-Cl, 5-$CF_3$ | 2-Cl, 5-SMe | 94–5 |
| 79 | H | H | 3-Cl, 5-$CF_3$ | 2-OEt | 167–8 |
| 80 | H | H | 3-Cl, 5-$CF_3$ | 2-$OCH_2$Ph | 134–5 |
| 81 | H | H | 3-Cl, 5-$CF_3$ | 2-OMe, 4-SMe | 162–3 |
| 82 | H | H | 3-Cl, 5-$CF_3$ | 2-Me, 5-$NO_2$ | 129–30 |
| 83 | benzyl | H | 3-Cl, 5-$CF_3$ | 2,6-$Cl_2$ | 164–8 |
| 84 | benzyl | H | 3-Cl, 5-$CF_3$ | 2-$NO_2$ | 147–9 |
| 85 | Me | H | 3-Cl, 5-$CF_3$ | 2,6-$Cl_2$ | 115–8 |
| 86 | Me | H | 3 Cl, 5-$CF_3$ | 2-$NO_2$ | oil |
| 87 | Me | H | 3-Cl, 5-$CF_3$ | 2-Cl, 6-F | 112–6 |
| 88 | H | H | 3-Cl, 5-$CF_3$ | 3-Me, 5-$NO_2$ | oil |
| 89 | H | H | 3-Cl, 5-$CF_3$ | 4-Me, 5-$NO_2$ | 152 |
| 90 | H | H | 3-Cl, 5-$CF_3$ | 2,5-$(OMe)_2$ | 165 |
| 91 | H | H | 3-Cl, 5-$CF_3$ | 2,3-$(OMe)_2$ | 117 |
| 92 | H | H | 3-Cl, 5-$CF_3$ | 2-OMe, 4-Cl | 200 |
| 93 | H | H | 3-Cl, 5-$CF_3$ | 2,4,5-$(OMe)_3$ | 184 |
| 94 | H | H | 3-Cl, 5-$CF_3$ | 2,4-$(CF_3)_2$ | 101 |
| 95 | H | H | 3-Cl, 5-$CF_3$ | 2-$NO_2$, 4-Cl | 116 |
| 96 | H | H | 3-Cl, 5-$CF_3$ | 2,3,4-$(OMe)_3$ | 125 |
| 97 | H | H | 3-Cl, 5-$CF_3$ | 2,5-$(CF_3)_2$ | 112 |
| 98 | H | H | 3-Cl, 5-$CF_3$ | 2-$NO_2$, 3-OMe | 149 |
| 99 | H | H | 3-Cl, 5-$CF_3$ | 2,4-$(NO_2)_2$ | 152 |
| 100 | H | H | 3-Cl, 5-$CF_3$ | 2,5-$Br_2$ | 136 |
| 101 | H | H | 3-Cl, 5-$CF_3$ | 2-$NO_2$, 5-OMe | oil |
| 102 | H | H | 3-Cl, 5-$CF_3$ | 2-Br, 3-$NO_2$ | 148 |
| 103 | H | H | 3-Cl, 5-$CF_3$ | 2-$NO_2$, 4-$CF_3$ | 138 |
| 104 | H | H | 3-Cl, 5-$CF_3$ | 2-Br, 5-$NO_2$ | 151 |

TABLE 1-continued (Ia)

| Cpd | R¹ | R² | (R³)$_q$ | (R⁴)$_p$ | m.p. (° C.) |
|---|---|---|---|---|---|
| 105 | H | H | 3-Cl, 5-CF₃ | 2-OPr | 122 |
| 106 | H | H | 3-Cl, 5-CF₃ | 2-(1-pyrrolyl) | oil |
| 107 | H | H | 3-Cl, 5-CF₃ | 2-Br, 5-Cl | 138 |
| 108 | H | H | 3-Cl, 5-CF₃ | 2-[(2-CN-phenyl)thio] | oil |
| 109 | H | H | 3-Cl, 5-CF₃ | 2-CN | 134 |
| 110 | H | H | 3-Cl, 5-CF₃ | 2-NO₂, 4,5-(OMe)₂ | 143–4 |
| 111 | H | H | 3-Cl, 5-CF₃ | 4-Me | 137–8 |
| 112 | H | H | 3-Cl, 5-CF₃ | 4-OMe | 148–9 |
| 113 | H | H | 3-Cl, 5-CF₃ | 4-CF₃ | 120–1 |
| 114 | H | H | 3-Cl, 5-CF₃ | 4-NO₂ | 115–6 |
| 115 | H | H | 3-Cl, 5-CF₃ | 3-NO₂ | 114–5 |
| 116 | H | H | 3-Cl, 5-CF₃ | 4-F | 78–9 |
| 117 | H | H | 3-Cl, 5-CF₃ | 3-NO₂, 4-Cl | 127–8 |
| 118 | H | H | 3-Cl, 5-CF₃ | 3,4-Me₂ | 128–9 |
| 119 | H | H | 3-Cl, 5-CF₃ | 3-Cl, 4-OMe | 122–3 |
| 120 | H | H | 3-Cl, 5-CF₃ | 4-CN | 108–10 |
| 121 | H | H | 3-Cl, 5-CF₃ | 3-CN | 122–3 |
| 122 | H | H | 3-Cl, 5-CF₃ | 3-CN, 4-OMe | 116–7 |
| 123 | H | H | 3-Cl, 5-CF₃ | 3-benzyloxy | oil |
| 124 | H | H | 3-Cl, 5-CF₃ | 3-phenoxy | 71–2 |
| 125 | H | H | 3-Cl, 5-CF₃ | 3-F | 123–4 |
| 126 | Me | H | 3-Cl, 5-CF₃ | 2-Cl | 99 |
| 127 | Me | H | 3-Cl, 5-CF₃ | 2,3-Me₂ | 124 |
| 128 | Me | H | 3-Cl, 5-CF₃ | 2-Br | 113 |
| 129 | Me | H | 3-Cl, 5-CF₃ | 3-Br | 105 |
| 130 | Me | H | 3-Cl, 5-CF₃ | 2-CF₃ | 100 |
| 131 | Me | H | 3-Cl, 5-CF₃ | 2,4,6-F₃ | 121 |
| 132 | Me | H | 3-Cl, 5-CF₃ | 2-I | 129 |
| 133 | Me | H | 3-Cl, 5-CF₃ | 2-F | semi-solid |
| 134 | Me | H | 3-Cl, 5-CF₃ | 2-Cl | 136 |
| 135 | Me | H | 3-Cl, 5-CF₃ | 2,6-F₂ | 111 |
| 136 | Me | H | 3-Cl, 5-CF₃ | 2,4-F₂ | 102 |
| 137 | Me | H | 3-Cl, 5-CF₃ | 2-CF₃, 5-F | 100 |
| 138 | Me | H | 3-Cl, 5-CF₃ | 3-CF₃, 2-F | oil |
| 139 | Me | H | 3-Cl, 5-CF₃ | 2-Me | 89 |
| 140 | Me | H | 3-Cl, 5-CF₃ | 4-NO₂ | 133 |
| 141 | benzyl | H | 3-Cl, 5-CF₃ | 2-Cl | 161 |
| 142 | benzyl | H | 3-Cl, 5-CF₃ | 2,3-Me₂ | 173 |
| 143 | benzyl | H | 3-Cl, 5-CF₃ | 2-Br | 157 |
| 144 | benzyl | H | 3-Cl, 5-CF₃ | 3-Br | 169 |
| 145 | benzyl | H | 3-Cl, 5-CF₃ | 2-CF₃ | 166 |
| 146 | benzyl | H | 3-Cl, 5-CF₃ | 2,4,6-F₃ | 154 |
| 147 | benzyl | H | 3-Cl, 5-CF₃ | 2-I | 174 |
| 148 | benzyl | H | 3-Cl, 5-CF₃ | 2-F | 127 |
| 149 | benzyl | H | 3-Cl, 5-CF₃ | 4-Cl | 197 |
| 150 | benzyl | H | 3-Cl, 5-CF₃ | 2,6-F₂ | 153 |
| 151 | benzyl | H | 3-Cl, 5-CF₃ | 2,4-F₂ | 129 |
| 152 | benzyl | H | 3-Cl, 5-CF₃ | 2-F, 3-CF₃ | 147 |
| 153 | benzyl | H | 3-Cl, 5-CF₃ | 3-F, 6-CF₃ | 182 |
| 154 | benzyl | H | 3-Cl, 5-CF₃ | 2-Me | 176 |
| 155 | benzyl | H | 3-Cl, 5-CF₃ | 4-NO₂ | 197 |
| 156 | benzyl | H | 3-Cl, 5-CF₃ | — | 199 |
| 157 | benzyl | H | 3-Cl, 5-CF₃ | 2-Cl, 6-F | 189 |
| 158 | H | H | 3-CF₃ | 2-NO₂ | 129–36 |
| 159 | H | H | 3-CF₃ | 2-Br | 95–8 |
| 160 | H | H | 3-CF₃ | 2-Cl | 108–10 |
| 161 | H | H | 3-CF₃ | 2-CF₃ | 110–15 |
| 162 | H | H | 3-CF₃ | 2-I | 126–36 |
| 163 | H | H | 3-CF₃ | 2-Cl, 6-F | 161–2 |
| 164 | H | H | 3-CF₃ | 2,6-F₂ | 142–6 |
| 165 | H | H | 3-CF₃ | 2,6-(OMe)₂ | 128–9 |
| 166 | H | H | 3-CF₃ | 2-CF₃, 5-F | 128–9 |
| 167 | H | H | 3-CF₃ | 2,4,6-Cl₃ | 181–4 |
| 168 | H | H | 3-CF₃ | 2,3,6-F₃ | 127–9 |
| 169 | H | H | 3-CF₃ | 2-Br, 6-Cl | 169–70 |
| 170 | H | H | 3-CF₃ | 2,6-Cl₂ | 169–71 |
| 171 | H | H | 3-Cl, 5-CF₃ | 2-Me, 6-NO₂ | 164–5 |
| 172 | H | H | 3-Cl, 5-CF₃ | 2,6-(OMe), 3-Cl | 177–8 |
| 173 | H | H | 3-Cl, 5-CF₃ | 2,6-(OMe)₂, 3-NO₂ | 184–5 |
| 174 | H | H | 3-Cl, 5-CF₃ | 2,3,5-Cl₃, 6-OH | 300–10 |
| 175 | H | H | 3-Cl, 5-CF₃ | 2,6-Cl₂, 3-OH | 96–8 |
| 176 | H | H | 3-Cl, 5-CF₃ | 2-Cl, 6-OH | 116–8 |
| 177 | Me | H | 3-Cl, 5-CF₃ | — | 110 |
| 178 | Me | H | 3-Cl, 5-CF₃ | 4-MeO | 146 |
| 179 | Me | H | 3-Cl, 5-CF₃ | 3,5-Cl₂ | 157 |
| 180 | Me | H | 3-Cl, 5-CF₃ | 2,4-Cl₂ | oil |
| 181 | H | H | 3-Cl, 5-CF₃ | 2-Cl, 6-MeS | 139–142 |
| 182 | H | H | 3-Cl, 5-CF₃ | 2-CH₂Cl | 92–3 |
| 183 | H | H | 3-Cl, 5-CF₃ | 2-(2-Br—Ph)CH₂S | oil |
| 184 | Et | H | 3-Cl, 5-CF₃ | 2,6-Cl₂ | 113–6 |
| 185 | Et | H | 3-Cl, 5-CF₃ | 2-Cl, 6-F | 116–8 |
| 186 | Et | H | 3-Cl, 5-CF₃ | 4-Cl | 90–2 |
| 187 | Et | H | 3-Cl, 5-CF₃ | 4-F | 78–80 |
| 188 | Pr | H | 3-Cl, 5-CF₃ | 2,6-Cl₂ | 121–3 |
| 189 | Pr | H | 3-Cl, 5-CF₃ | 2-Cl, 6-F | 110–2 |
| 190 | Pr | H | 3-Cl, 5-CF₃ | 4-Cl | 88–90 |
| 191 | Pr | H | 3-Cl, 5-CF₃ | 4-F | 113–5 |
| 192 | Pr | H | 3-Cl, 5-CF₃ | 2,4-Cl₂ | oil |
| 193 | Pr$^i$ | H | 3-Cl, 5-CF₃ | 2,4-Cl₂ | 148–52 |
| 194 | H | H | 3-Cl, 5-CF₃ | 4-BuO | 100–3 |
| 195 | H | H | 5-cyano | 2,6-Cl₂ | 176–8 |
| 196 | H | H | 5-cyano | 2-Cl, 6-F | 171–3 |
| 197 | H | H | 5-cyano | 2-Br, 6-Cl | 159–61 |
| 198 | H | H | 5-cyano | 2-NO₂ | 151–3 |
| 199 | H | H | 5-cyano | 4-Cl | 116–8 |
| 200 | H | H | 3-Cl, 5-CF₃ | 2-phthalimido | 173–4 |
| 201 | Me | H | 3-Cl, 5-CF₃ | 4-BuO | 94–5 |
| 202 | H | H | 5-OCOMe | 2,6-Cl₂ | 153–4 |
| 203 | H | H | 5-OCOMe | 2-Cl, 6-F | 137–8 |
| 204 | H | H | 5-OCOMe | 2-Br, 6-Cl | 158–9 |
| 205 | H | H | 5-OCOMe | 2-I | 144–5 |
| 206 | H | H | 5-OCOEt | 2,6-Cl₂ | 98–100 |
| 207 | H | H | 5-OCOEt | 2-Br, 6-Cl | 96–8 |
| 208 | H | H | 5-OCOEt | 2-Cl, 6-F | 97–9 |
| 209 | H | H | 5-OCOEt | 4-Cl | 112–4 |
| 210 | H | H | 5-OCOEt | 2-Cl | 84–7 |
| 211 | H | H | 5-OCOEt | 2-NO₂ | 85–9 |
| 212 | H | H | 5-OSO₂Me | 2,6-Cl₂ | 132–3 |
| 213 | H | H | 6-OH | 2,6-Cl₂ | 269–70 |
| 214 | H | H | 6-Me-3-OSO₂Me | 2,6-Cl₂ | 185–6 |
| 215 | H | H | 6-Cl | 2,6-Cl₂ | 139–41 |
| 216 | H | H | 4-Cl | 2,6-Cl₂ | 156–7 |
| 217 | Pr$^i$ | H | 3-Cl, 5-CF₃ | 2,6-Cl₂ | 135–7 |
| 218 | NC—CH₂ | H | 3-Cl, 5-CF₃ | 2,6-Cl₂ | 160–3 |
| 219 | NC—CH₂ | H | 3-Cl, 5-CF₃ | 2-Cl, 6-F | 155–6 |
| 221 | NC—CH₂ | H | 3-Cl, 5-CF₃ | 4-Cl | 118–9 |
| 222 | NC—CH₂ | H | 3-Cl, 5-CF₃ | 3,5-Cl₂ | 122–4 |
| 223 | NC—CH₂ | H | 3-Cl, 5-CF₃ | 2,4-Cl₂ | 110–2 |

EXAMPLE 5

N-[1-(3-Chloro-1-trifluoromethyl-2-pyridyl)-2,4-dichlorobenzenesulfonamide (Compound 501)

Triethylamine (0.28 ml) was added to a suspension of (3-chloro-5-trifluoromethyl-2-pyridyl)methylamine hydrochloride (0.25 g) in tetrahydrofuran (6 ml). After 15 minute, the white suspension was filtered and washed with tetrahydrofuran. The filtrate and washings were added to 2,4-dichlorobenzenesuifonyl chloride (0.25 g) and the mixture stirred overnight at room temperature, water added and stirred for 30 minutes. The white solid, which formed, was collected. This was the title product, m.p. 125–6° C. (Compound 501)

In a similar manner, the following compounds of general formula Ia were obtained. The table includes the compound described in the previous Example.

(Ia)

| Cpd | $(R^4)_p$ | m.p. (° C.) |
|---|---|---|
| 501 | 2,4-Cl$_2$ | 125–6 |
| 502 | 4-Me | 113–4 |
| 503 | 2-Cl | 114–5 |
| 504 | 2-Cl, 4-F | 99–101 |
| 505 | 2-F | 126–8 |
| 506 | 2,3-N=CH—CH=CH— | 145–6 |
| 507 | 2-CN | 154–7 |
| 508 | 2-Br | 134–6 |
| 509 | 2,6-Cl$_2$ | 160–1 |
| 510 | 2,5-(OMe)$_2$ | 119–23 |
| 511 | 2,6-F$_2$ | 141–3 |
| 512 | 2-Cl-6-Me | 170–2 |
| 513 | 2-NO$_2$ | 116–8 |
| 514 | 6-Me-3-NO$_2$ | 113–5 |
| 515 | 2,3-CH=CH—CH=CH— | 94–5 |
| 516 | 2,4-F$_2$ | 93–5 |
| 517 | 2,5-Cl$_2$ | 92–3 |
| 518 | 3,4-Cl$_2$ | 117–8 |
| 519 | 5-Cl-2-MeO | 94–5 |
| 520 | 2,4,6-Cl$_3$ | 137–9 |
| 521 | 4-Cl-2,5-Me$_2$ | 130–2 |
| 522 | 2,4-Cl$_2$-5-Me | 155–7 |
| 523 | 4-Cl | 132–3 |
| 524 | 2,3-Cl$_2$ | 104–6 |
| 525 | 2-CF$_3$ | 102–4 |
| 526 | — | 99–100 |
| 527 | 3-PhO | 88–9 |
| 528 | 3,4-(OMe)$_2$ | 126–7 |
| 529 | 3,5-Cl$_2$ | 125–7 |
| 530 | 5-F-2-Me | 88–9 |

EXAMPLE 6

Ethyl 2-(3-Chloro-5-trifluoromethyl-2-pyridyl)-N-(3,4-dimethoxybenzoyl)glycinate (Compound 601)

Triethylamine (0.28 ml) was added to a solution of ethyl 2-(3-chloro-5-trifluoromethyl-2-pyridyl)glycinate (1 g; prepared in a similar manner to the starting material for Example 3) in dimethylformamide (10 ml) with stiring followed by 3,4-dimethoxybenzoyl chloride (0.70 g). the mixture was stirred for 45 minutes and evaporated. The residue was extracted with ethyl acetate and the extracts worked up to give the title product, m.p. 40–3° C. (Compound 601)

In a similar manner to one of the previous Examples, the following compounds in Table 3 of general formula Ic were obtained. The table includes the compound described in the previous Example.

TABLE 3

(Ic)

| Cpd | $Q^Z$ | $R^2$ | L | $(R^4)_p$ | m.p. (° C.) |
|---|---|---|---|---|---|
| 601 | H | H | —C(=O)— | 3,4-Me$_2$ | 40–3 |
| 602 | H | benzyl | —C(=O)— | 4-MeO | 116–9 |
| 603 | H | H | —C(=O)— | 2,4-Cl$_2$ | 107–10 |
| 604 | H | H | —SO$_2$— | 3,4-Cl$_2$ | 89–92 |
| 605 | H | H | —C(=O)— | — | oil |
| 606 | H | H | —C(=O)— | 2-Me | oil |
| 607 | H | H | —C(=O)— | 4-MeO | 91–4 |
| 608 | H | H | —C(=O)— | 3-NO$_2$ | oil |
| 609 | H | H | —C(=O)— | 4-tert-butyl | oil |
| 610 | H | H | —C(=O)— | 2-CF$_3$ | oil |
| 611 | H | H | —C(=O)— | 2,6-Cl$_2$ | oil |
| 612 | H | H | —SO$_2$— | 3-CF$_3$ | 74–6 |
| 613 | H | H | —C(=O)— | 2-F | oil |
| 614 | H | H | —C(=O)— | 2-Cl | oil |
| 615 | H | H | —C(=O)— | 3-Br | 62–4 |
| 616 | H | H | —SO$_2$— | 2,5-Cl$_2$ | oil |
| 617 | H | ethyl | —C(=O)— | — | oil |
| 618 | H | ethyl | —C(=O)— | 2-Cl | oil |
| 619 | H | ethyl | —C(=O)— | 3-NO$_2$ | oil |
| 620 | H | ethyl | —C(=O)— | 4-MeO | oil |
| 621 | H | H | —C(=O)— | 2-Br | 155–6 |
| 622 | H | H | —C(=O)— | 3,4-(OMe)$_2$ | 40–3 |
| 623 | H | benzyl | —C(=O)— | 4-MeO | 116–9 |

EXAMPLE 7

N-[(3-Chloro-5-trifluoromethyl-2-pyridyl)methyl]-2-chlorobenzenethioamide (Compound 701)

A solution of compound 23, (3.84 g) and Lawesson's reagent (4.45 g) in toluene (50 ml) was heated at 80° C. for 1 hour. The mixture was purified by silica gel chromatography to give to give the title compound, m.p. 102–3° C.

In a similar manner the following compounds were obtained. The table includes the compund described in the previous Example.

| Cpd | $R^1$ | $(R^4)_p$ | m.p. (° C.) |
|---|---|---|---|
| 701 | H | 2-Cl | 102–5 |
| 702 | H | 4-Me | 97–9 |
| 703 | H | 3-Me | 72–5 |
| 704 | H | 2-MeO | 172–5 |
| 705 | H | 3-MeO | 86–8 |
| 706 | H | 4-MeO | 107–9 |
| 707 | H | 3-Cl | 92–5 |
| 708 | H | 4-Cl | 123–5 |
| 709 | H | 4-Me$_2$N | 145–7 |
| 710 | H | 3-EtO | 62–4 |
| 711 | H | 4-EtO | 115–8 |

-continued

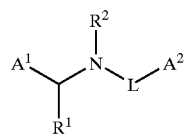

| Cpd | R¹ | (R⁴)ₚ | m.p. (° C.) |
|---|---|---|---|
| 712 | H | 3-NO₂ | 108–9 |
| 713 | H | 4-tert-butyl | 88–91 |
| 714 | H | 4-NO₂ | 190–2 |
| 715 | H | 4-PrO | 95–8 |
| 716 | H | 4-PrⁱO | 86–8 |
| 717 | H | 3-Cl, 4-MeO | 147–9 |
| 718 | H | 3-BuO | oil |
| 719 | H | 3-Cl, 4-Me₂N | 107–9 |
| 720 | H | 4-Br | 122–4 |
| 721 | H | 3,4,5-(OMe)₃ | 132–3 |
| 722 | Me | 3-Me | 119–21 |
| 723 | Me | 3-MeO | 107–8 |
| 724 | Me | 4-MeO | 122–3 |
| 725 | Me | 2-Cl | 114–5 |
| 726 | Me | 3-Cl | 112–5 |
| 727 | Me | 4-Cl | 127–9 |
| 728 | Me | 3-EtO | 100–1 |
| 729 | Me | 4-EtO | 101–4 |
| 730 | Me | 3-NO₂ | 117–9 |
| 731 | Me | 4-tert-butyl | 112–4 |
| 732 | Me | 4-NO₂ | 246–8 |
| 733 | Me | 4-PrO | 97–8 |
| 734 | Me | 4-PrⁱO— | 92–3 |
| 735 | Me | 3-Cl, 4-MeO | 103–5 |
| 736 | Me | 3-BuO | 73–6 |
| 737 | Me | 3-Cl, 4-Me₂N | 85–8 |
| 738 | Me | 4-Br | 140–2 |
| 739 | Me | 3,4,5-(OMe)₃ | 118–120 |
| 740 | H | 2-Me | 101–4 |
| 741 | H | 2,3-CH=CH—CH=CH— | 154–6 |
| 742 | H | 4-BuO | 76–80 |
| 743 | H | 4-PhCH₂O— | 110–4 |
| 744 | Me | 4-Me | 134–5 |
| 745 | Me | 2-MeO | 109–12 |
| 746 | Me | 4-Me₂N | 177–80 |
| 747 | Me | 2,3-CH=CH—CH=CH— | 123–5 |
| 748 | Me | 4-BuO | 100–3 |
| 749 | Me | 4-PhCH₂O— | 132–4 |

TEST EXAMPLE

Compounds are assessed for activity against one or more of the following:

*Phytophthora infestans*: late blight
*Plasmopara viticola*: vine downy mildew
*Erysiphe graminis f.* sp. *tritici*: wheat powdery mildew
*Pyricularia oryzae*: rice blast
*Leptosphaeria nodorum*: glume blotch
*Botrytis cinerea*: grey mould An aqueous solution of the compound at the desired concentration, including a wetting agent, was applied by spray or by drenching the stem base of the test plants, as appropriate. After a given time, plants or plant parts were inoculated with appropriate test pathogens before or after application of the compounds as appropriate, and kept under controlled environmental conditions suitable for maintaining plant growth and development of the disease. After an appropriate time, the degree of infection of the affected part of the plant was visually estimated. The compound was assessed on a score of 1 to 3 where 1 is little or no control, 2 is moderate control and 3 is good to total control. At a concentration of 500 ppm (w/v) or less, the compound scored 2 or more against the above fungi.

*Phytophthora infestans*
1, 3, 6, 8, 13, 14, 17–21, 22, 23, 25, 27, 29, 31–34, 37–46, 59, 62–64, 66, 68–71, 85, 87, 95, 98, 101, 107, 110, 122–124, 128, 130, 132, 171, 173, 180 and 701.

*Plasmopara viticola*
1, 3, 13, 14, 15, 17–21, 22, 23, 25, 27, 29, 31–34, 37, 39,41–46, 59, 63,64, 66, 69, 71, 84, 86, 87, 102–110, 124, 128, 130, 132, 150 and 171.

*Erysiphe graminis f.* sp. *tritici*
16, 25, 28, 146, 147, 148, 151, 155, 156, 165, 150 and 151.

*Pyricularia oryzae*
16, 25, 31, 38, 41, 45, 65, 89. 97, 146, 157, 169, 150, 151, 152, 156, 158 and 176.

*Leptosphaeria nodorum*
15, 16, 18, 22, 33, 34, 92, 63. 128, 130, 143, 149 and 150.

*Botrytis cinerea*
35 127, 130, 134 and 139.

What is claimed is:

1. A compound of formula I or a salt thereof $$A^1 \underset{R^1}{\overset{R^2}{\underset{|}{\text{—}}}} N \underset{L}{\text{—}} A^2$$

wherein A¹ is a 2-pyridyl group having substituents at the three or five position, or both, and at no other position, R¹ and R² are hydrogen, L is —(C=O)—, —SO₂— or —(C=S)— and A² is substituted phenyl, wherein any A¹ substituent is selected from the group consisting of halogen, hydroxy, cyano, nitro, SF₅, trialkylsilyl, optionally substituted amino, E, OE or SE, where E is alkyl, alkenyl, alkynyl, cycloalkyl, cycloalkenyl, phenyl, each of which is optionally substituted, or —C(E)=N—Q, where Q is E, OE, SE or optionally substituted amino, and wherein the optional substituent when present on any alkyl, alkenyl, alkynyl, cycloalkyl, cycloalkenyl or cycloalkynyl moiety is selected from the group consisting of halogen, cyano, alkoxy, alkylthio, mercapto, hydroxy, nitro, amino, acyl, acyloxy, acylthio, phenyl, phenylthio, phenoxy, when present on any cycloalkyl, cycloalkenyl or cycloalkynyl is an alkyl, alkenyl or alkynyl, when present on any phenyl group are selected from the same group as the A¹ substituents, and when present on any amino group is E or acyl.

2. A compound according to claim 1 in which A² is phenyl substituted with halogen.

3. A compound according to claim 1 in which L is —(C=O)—.

4. A compound according to claim 3 in which A¹ is 2-pyridyl substituted by at least one member of the group consisting of fluorine, chlorine, bromine, iodine, trifluoromethyl, nitro and methoxy and A² is phenyl substituted with halogen.

5. A method of combating phytopathogenic fungi, at a locus infested or liable to be infested therewith, which comprises applying to the locus a compound of formula I or a salt thereof

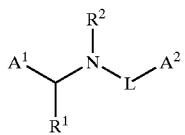

wherein
$A^1$ is substituted 2-pyridyl;
$A^2$ is substituted phenyl;
L is —(C=O)—, —SO$_2$— or —(C=S)—;
$R^1$ is hydrogen, optionally substituted alkyl or acyl; and
$R^2$ is hydrogen or optionally substituted alky.

6. The method of claim 5, in which $A^1$ is a 2-pyridyl group having substituents at the 3 or 5 positions, or both, and at no other position, and $R^1$ and $R^2$ are hydrogen.

7. A method according to claim 6 in which $A^2$ is phenyl substituted with halogen.

8. A method according to claim 6 in which L is —(C=O)—.

9. A method according to claim 8 in which $A^1$ is 2-pyridyl substituted by at least one member of the group consisting of fluorine, chlorine, bromine, iodine, trifluoromethyl, nitro and methoxy and $A^2$ is phenyl substituted with halogen.

* * * * *